(12) United States Patent
Plank et al.

(10) Patent No.: US 7,595,513 B2
(45) Date of Patent: Sep. 29, 2009

(54) SEMICONDUCTOR RADIATION SOURCE AND LIGHT CURING DEVICE

(75) Inventors: Wolfgang Plank, Rankwell (AT); Bruno Senn, Buchs (CH)

(73) Assignee: Ivoctar Vivadent AG, Schaan (LI)

( * ) Notice: Subject to any disclaimer, the term of this patent is extended or adjusted under 35 U.S.C. 154(b) by 273 days.

(21) Appl. No.: 11/728,252

(22) Filed: Mar. 23, 2007

(65) Prior Publication Data
US 2007/0228516 A1 Oct. 4, 2007

(30) Foreign Application Priority Data
Apr. 3, 2006 (DE) .................. 10 2006 015 335

(51) Int. Cl.
*H01L 33/00* (2006.01)
(52) U.S. Cl. ........................................ 257/98
(58) Field of Classification Search ............ 257/79–85, 257/95, 98, E33.056–E33.059; 438/29–31
See application file for complete search history.

(56) References Cited

U.S. PATENT DOCUMENTS

| 5,122,943 | A | 6/1992 | Pugh |
| 5,130,761 | A | 7/1992 | Tanaka |
| 6,095,812 | A | 8/2000 | Senn et al. |
| 6,930,332 | B2 | 8/2005 | Hashimoto |
| 7,008,078 | B2 | 3/2006 | Shimizu et al. |
| 7,078,728 | B2 * | 7/2006 | Ishii et al. ............. 257/79 |
| 7,345,322 | B2 * | 3/2008 | Kikuchi ............. 257/99 |
| 2002/0177099 | A1 | 11/2002 | Cao |
| 2004/0218390 | A1 | 11/2004 | Holman |
| 2005/0002191 | A1 | 1/2005 | Shimizu et al. |
| 2005/0152146 | A1 | 7/2005 | Owen et al. |
| 2006/0001361 | A1 | 1/2006 | Imai et al. |
| 2006/0012988 | A1 | 1/2006 | Hsieh et al. |
| 2007/0102722 | A1 * | 5/2007 | Ishizaka et al. ............. 257/99 |
| 2008/0031009 | A1 * | 2/2008 | Kodaira et al. ............. 362/612 |

FOREIGN PATENT DOCUMENTS

| DE | 89 07 530 U1 | 9/1989 |
| DE | 100 37 420 A1 | 1/2002 |
| DE | 10 2005 028 176 A1 | 2/2006 |
| EP | 0 509 389 A2 | 10/1992 |
| EP | 0 802 572 A2 | 10/1997 |
| EP | 0 879 582 A2 | 11/1998 |
| GB | 2 197 126 A | 5/1988 |
| WO | WO 2005/067063 A1 | 7/2005 |

* cited by examiner

*Primary Examiner*—Calvin Lee
(74) *Attorney, Agent, or Firm*—John C. Thompson; Alan S. Korman; Sandra J. Thompson (57) ABSTRACT

Provision is made of a semiconductor radiation source having a base body on which at least two LED chips are mounted, at least one chip of which is connected to a series resistor which can be adjusted. The LED chips (12, 14) are fitted to the base body (24) using a thermally conductive connection and at least one printed circuit board (30) which bears the series resistor (40, 42) is also mounted on the base body (24).

27 Claims, 8 Drawing Sheets

SEMICONDUCTOR RADIATION SOURCE AND LIGHT CURING DEVICE

CROSS-REFERENCE TO RELATED APPLICATIONS

This application claims foreign priority benefits under 35 U.S.C. §119 from German patent application Ser. No. 10 2006 015 335.9 filed Apr. 3, 2006.

TECHNICAL FIELD

The invention relates to a semiconductor radiation source having a base body on which at least two LED chips are mounted, and, more particularly to a semiconductor radiation source having at least two LED chips wherein at least one chip is connected to a series resistor which can be adjusted.

BACKGROUND OF THE INVENTION

Semiconductor radiation sources have been known for a long time. They may have light-emitting diodes or LEDs whose emission spectrum can be adapted to the requirements as regards the sensitivity spectrum of the materials to be cured by appropriately selecting the LEDs.

Light curing devices must be calibrated, as has already been disclosed, for example, in U.S. Pat. No. 6,095,812. On the other hand, the practice of calibrating light-emitting diodes, which are connected in parallel with one another, using series resistors has also already been disclosed, as regards which reference may be made, for example, to DE 100 37 420. In this solution, the LED chips are arranged in a type of matrix and the respective associated series resistors can be adjusted by means of laser trimming.

When implementing light curing devices, it is desirable to provide particularly high light emission at precise points in order to rapidly provide the through-curing in the desired quality. In this respect, it has been disclosed to combine light-emitting diodes in a closely adjacent manner and to focus the light emitted by the light-emitting diodes using suitable optical measures such as a converging lens.

On the other hand, this raises the problem of sufficient cooling especially in the case of high-power light-emitting diodes and LED chips. Sufficient cooling can, in practice, only be provided by directly applying the LED chips to a base body as a heat sink which has been intensively prepared for heat dissipation.

Nevertheless, the surroundings of the LED chips are really hot, with the result that it must also be ensured, for example, that the converging lens which usually comprises plastic is not inadvertently deformed.

Resistors frequently comprise a layer-like carrier material with graphite incorporations. The desired resistance can be set within wide ranges by selecting the thickness and other dimensions of the resistance layer; the resistance value can be selected to be of virtually any desired order of magnitude (from the m range to the T range) by selecting the mixture which is provided for the resistance track or layer.

It has already been proposed to centrally arrange the LED chips on a heat sink using dense packing and to arrange resistance layers outside this region. An attempt has been made, by laser-trimming the resistors, to bring the power of the individual LED chips more into line with one another. During operation, LED chips of this type nevertheless frequently exhibit an uneven power distribution which is unsatisfactory and could not really be eliminated even by repeated readjustment.

OBJECTS AND SUMMARY OF THE INVENTION

The inventive measure of arranging series resistors for the LED chips on a printed circuit board surprisingly results in a greatly improved calibration result. It is obviously important for the calibration accuracy that the series resistors are not subjected to excessive temperature fluctuations especially since carbon film resistors have a negative temperature coefficient, i.e. the resistance value of resistance layers which are intended to be small becomes even smaller as a result of heating and thus becomes too small.

Arranging the series resistors on a printed circuit board surprisingly results in far better adjustment of the LED chips as regards their light emission. The light-emitting diode chips can therefore be operated closer to their limiting value, with the result that the luminous efficiency increases overall and the through-curing result is thus improved.

Arranging the series resistors on the printed circuit board makes it possible to arrange the LED chips as compactly as possible and to remove the series resistors from the optical region, with the result that adjustment is considerably simplified, for example by means of laser trimming.

At the same time, the printed circuit board may form a thermally stable support for a supporting element for a lens such as a cover lens or a converging lens, with the result that there is no need to use particularly thermally stable materials for the supporting element. This also reduces the introduction of heat into the lens itself, with the result that, even in the case of high optical power and thus high heat emission of the LED chips, there is no risk of the lens being damaged.

In order to nevertheless arrange the LED chips at the most favorable distance in front of the first lens, the cover lens, it may be desirable to leave a projection in the base body which holds the LED chips. The printed circuit board may then be situated at the same height as the LED chips, which is favorable for bonding.

It is also particularly favorable if contact areas of the printed circuit board project into the optical region, that is to say the region within the supporting element for the lens. Bonding can then be implemented in a particularly simple manner, and the power supply for the LED chips is ensured using conductor tracks which are known per se, it being possible to provide a common ground contact area for a plurality of LED chips or else for all of the LED chips, with the result that, for a number n of LED chips, only n+1 contact areas and a corresponding number of conductor tracks are required.

Each LED chip is preferably assigned a corresponding series resistor, and adjustment is effected in a manner known per se by selectively applying voltage to the corresponding current path during simultaneous laser trimming.

In particular cases, a number of n−1 series resistors may also suffice.

The conductor tracks are preferably arranged on the top side of the printed circuit board, with the result that the series resistors can be directly fitted there using suitable technology. The series resistors themselves can be implemented using thick-film technology, thin-film technology or, if appropriate, may also be implemented in the form of discrete series resistors and series resistors which have been soldered on, series resistors which can be trimmed in a simple manner being preferred.

One advantageous refinement provides for the entire conductor track, that is to say including the series resistors but not the bonding areas for the LED chips, to be provided, after trimming, with a protective resist in order to prevent the resistance values being influenced by ambient influences.

The supporting element for the lens may then also be readily supported on conductor tracks which are protected by the protective resist, but it is also possible to provide supporting stubs outside the region of the conductor track, with the result that the supporting element is supported only there.

Another advantageous refinement provides for the LED chips to be adjacent to one another and to be arranged in a central region of the base body.

Another advantageous refinement provides for the printed circuit board to be arranged between the edge of the base body and the LED chips.

Another advantageous refinement provides for a first LED chip to be arranged on an optical axis and for a plurality of further LED chips to be radially arranged outside the first LED chip, in particular in such a manner that they are symmetrical with respect to one another and surround the first LED chip in the manner of a cross or star.

Another advantageous refinement provides for a total of four further LED chips to surround the first LED chip.

Another advantageous refinement provides for a reflector element which is supported on the base body and/or the printed circuit board and/or the LED chips to be arranged between two mutually adjacent LED chips.

Another advantageous refinement provides for the reflector element to have two reflecting areas which run essentially obliquely, each reflecting area reflecting radiation emanating from the adjacent LED chip.

Another advantageous refinement provides for the reflecting areas, when viewed in the direction of the optical axis, to essentially extend in a manner corresponding to the height of the printed circuit board or to project beyond the printed circuit board and to be, in particular, of slightly concave or parabolic shape.

Another advantageous refinement provides for a plurality of reflector elements to be connected to one another so as to form a grating reflector, the grating reflector, in particular, being supported on the base body and/or the printed circuit board and/or the LED chips.

Another advantageous refinement provides for the LED chips to be fitted in a central region of the base body, essentially at the height of the printed circuit board.

Another advantageous refinement provides for radiation absorbers which are connected, in particular, to the base body using thermally conductive connections to extend between LED chips, in particular external LED chips, and the printed circuit board.

Another advantageous refinement provides for the radiation absorbers to be simultaneously of heat-insulating design and to be composed of ceramic, in particular.

Another advantageous refinement provides for the radiation absorbers to extend at least over the width of the LED chips and, in particular, to have a greater height than the LED chips, preferably approximately 1.5 to 5 times the height, and particularly preferably approximately twice the height, of the LED chips.

Another advantageous refinement provides for a cover lens to be arranged in the beam path downstream of the LED chips and for an annular or tubular spacer to be provided for said lens, and for the spacer to be supported on the printed circuit board and/or the base body.

Another advantageous refinement provides for a closed space which has a transparent or translucent liquid or gelatinous substance, in particular silicone gel or a potting compound, to extend between the LED chips, the spacer and the cover lens.

Another advantageous refinement provides for the substance to have phosphorus particles.

Another advantageous refinement provides for at least one conductor track of the printed circuit board to run through under the spacer.

Another advantageous refinement provides for the series resistors) to be fitted such that it/they is/are freely accessible outside the supporting element and for it/them to be able to be adjusted there.

Another advantageous refinement provides for the series resistor(s) to be connected, in particular soldered, to the printed circuit board via resistance contact areas.

Another advantageous refinement provides for the series resistor(s) to be in the form of a resistance track whose width can be adjusted, in particular reduced, at at least one point, for example by means of laser trimming.

Another advantageous refinement provides for the series resistor to be printed onto the printed circuit board or to be applied using thick-film technology and to have, in particular, a compound or paste containing conductive particles, in particular composed of graphite.

Another advantageous refinement provides for that side of the cover lens which faces the LED chips to be of essentially planar or convex or concave design.

Another advantageous refinement provides for the base body to be at least partially composed of copper and/or to be at least partially coated with gold or nickel/gold.

Another advantageous refinement provides for a converging lens whose diameter is, in particular, larger than the diameter of the cover lens to be arranged in the beam path downstream of the cover lens.

Another advantageous refinement provides for a reflector to be arranged in the beam path downstream of the LED chips at a distance from the latter and to also be arranged, in particular, downstream of the cover lens in the beam path.

Another advantageous refinement provides for a light guide to be arranged in the beam path downstream of the reflector.

Another advantageous refinement provides for the LED chips to emit light at different wavelengths.

Another advantageous refinement provides for the LED chips to emit light at the same wavelengths.

Another advantageous refinement provides for the printed circuit board to also extend, in particular, into the areas located between the limbs of the cross.

Another advantageous refinement provides for the light curing device to be in the form of a hand-held device having a handle.

Another advantageous refinement provides for the light curing device to have a housing on which the converging lens is supported.

BRIEF DESCRIPTION OF THE FIGURES

Further advantages, details and features emerge from the following description of a plurality of exemplary embodiments with reference to the drawing, in which.

DETAILED DESCRIPTION

Figure 1:
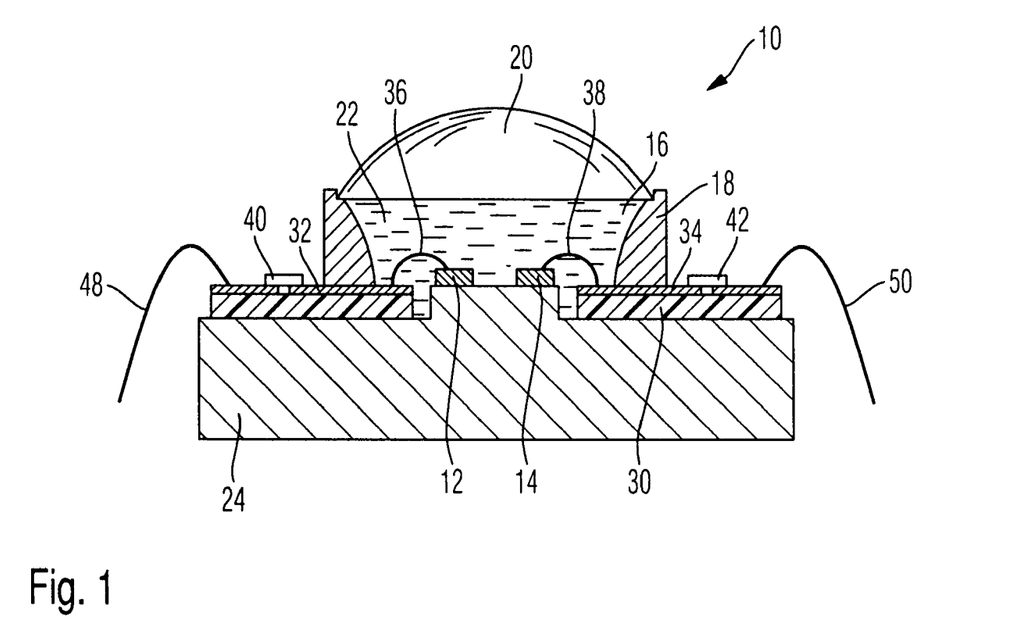
FIG. 1 shows a partially diagrammatic illustration of a section through a first embodiment of an inventive radiation source as part of an inventive light curing device.

The semiconductor radiation source 10 illustrated in FIG. 1 has a plurality of LED chips 12, 14 (two chips in the exemplary embodiment illustrated). The chips are held in an internal space 16 which is surrounded by a supporting element 18 for a lens 20. The lens 20 is mounted and sealed on a circumferential bearing shoulder of the supporting element. In the exemplary embodiment illustrated, the internal space 16 is filled with a transparent medium 22.

The LED chips 12, 14 are permanently fitted to a base body 24 using a thermally conductive connection. The base body may be composed of copper, for example, and the chips may be adhesively bonded using an adhesive having a strength of a few micrometers, with the result that there is an extremely low thermal resistance which also permits high-power LED chips.

The invention provides for the LED chips 12 and 14 to be arranged such that they are surrounded by a printed circuit board. The printed circuit board is fastened to the base body in a very simple manner, for example using a double-sided adhesive tape. It goes without saying that, instead of this, any other desired suitable type of fastening is also possible, for example also using screws, rivets or the like.

In a manner known per se, the printed circuit board 30 has conductor tracks which either extend on the top side of said printed circuit board or within the latter, also on the underside in isolated cases. The conductor tracks which are preferably arranged on the top side of the printed circuit board terminate in connecting areas such that they are adjacent to the LED chips 12 and 14. Bonding pads are formed there, and the LED chips 12 and 14 and these connecting areas of the conductor tracks 32 and 34 are connected using bonding wires 36 and 38. In this respect, the connecting areas, the bonding wires 36 and 38 and the LED chips 12 and 14 are held entirely in the internal space 16. The internal space 16 may be filled with any desired suitable medium, for example with a potting compound having phosphorus particles which are excited by the light radiation emitted by the LED chips.

In the exemplary embodiment illustrated, the supporting element 18 is supported on the printed circuit board 30. As a result of this refinement, said supporting element is thermally insulated to an improved extent from the base body 24 which is heated by the LED chips 12 and 14, and lower thermal stresses are introduced into the lens 20.

According to the invention, the conductor tracks 32 and 34 extend through to the outside under the supporting element 18. Respective series resistors 40, 42 are provided there, a respective series resistor 40, 42 being connected to an LED chip 12, 14. The connection is effected using the respective associated conductor track 32 or 34, that is to say under the supporting element 18.

In this solution, the series resistor 40, 42 is in the form of a respective series resistor which can be adjusted and is soldered onto the printed circuit board via corresponding connecting panels in the course of the conductor tracks 32 and 34. For example, each series resistor may comprise a resistance track, for example comprising a ceramic body which has a graphite layer applied to it and can be adjusted using laser trimming.

According to the invention, adjustment is then effected in such a manner that the LED chips 12 and 14 are adjusted using laser trimming after the inventive radiation source has been completed. To this end, the optical power of each individual light source, that is to say of the LED chips 12 and 14, for example, is measured in this case by alternately switching said light sources on and correspondingly adjusting them in the desired manner.

In this connection, it is particularly favorable for adjustment to be effected after the lens 20 has already been applied and the potting compound has also been filled into the internal space 16. Any unevenness in the optical media can thereby additionally be readily included in the adjustment process.

Implementing a lens having a planar underside and a convex top side makes it possible to bring the lens very close to the region of the LED chips in order to realize a favorable emission characteristic.

Figure 2:
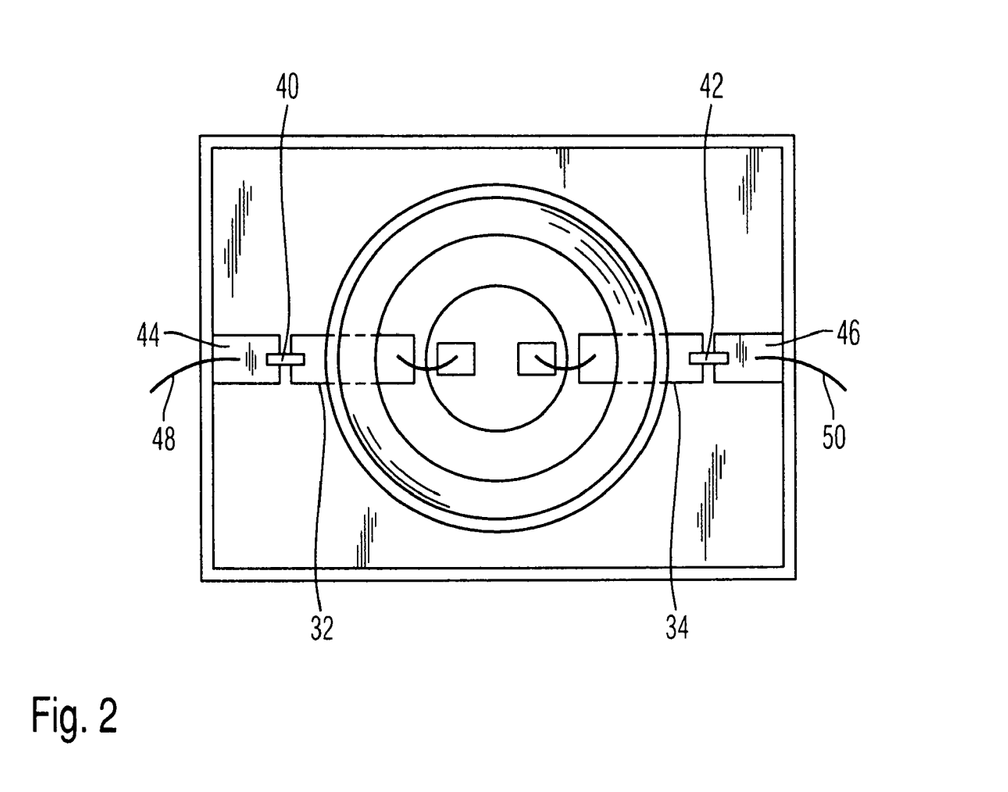
FIG. 2 shows the plan view of the embodiment shown in FIG. 1.

The solution shown in FIG. 1 can be seen in the plan view in FIG. 2. The same reference symbols refer to the same parts here and in the further FIGS. It can be seen that further connecting tracks 44 and 46 which are connected to connecting wires 48 and 50 that are used to supply power to the LED chips extend on the far side of the series resistors 40 and 42. This solution provides for the base body 24 to be used as a common ground, which is not specifically illustrated in FIGS. 1 and 2.

Figure 3:
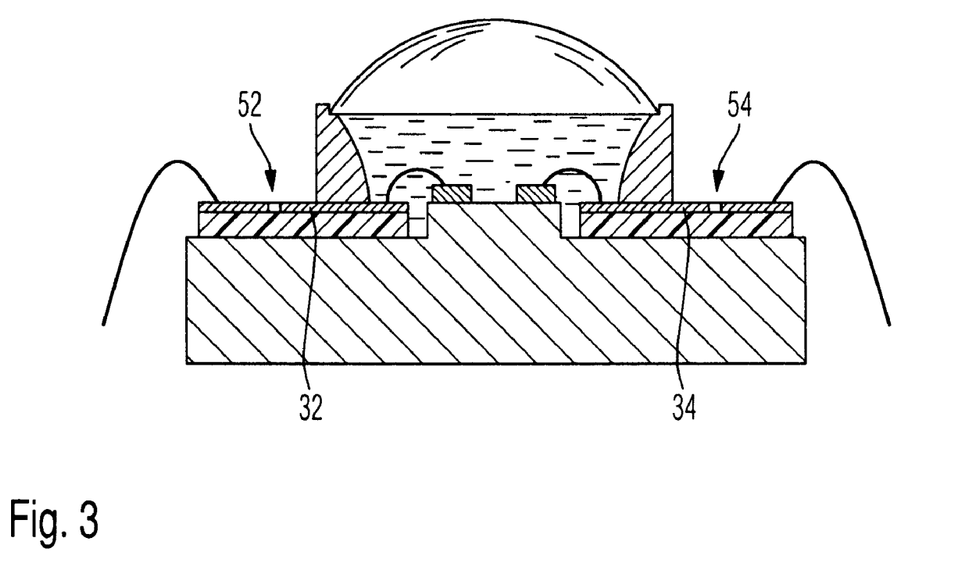
FIG. 3 shows a section through another embodiment in an illustration corresponding to the illustration shown in FIG. 1.
Figure 4:
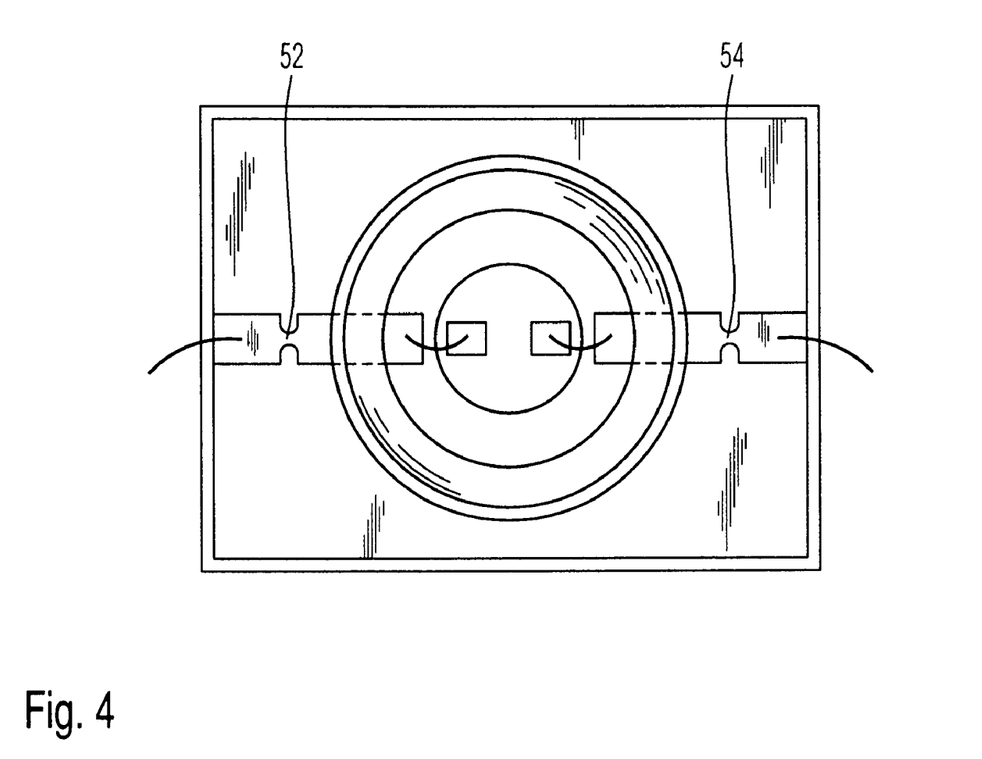
FIG. 4 shows a plan view of the embodiment shown in FIG. 3.

A modified refinement of the inventive semiconductor radiation source can be seen in FIGS. 3 and 4. In this solution, the discrete series resistor 40 and 42 has respectively been replaced with a constriction 52, 54 of the relevant conductor track 32, 34, the conductor track 32, 34 then being composed in this case of a respective material having a somewhat higher resistance. The respective series resistor which has been implemented can be adjusted within wide ranges using the depth of the constriction 52, 54.

Figure 5:
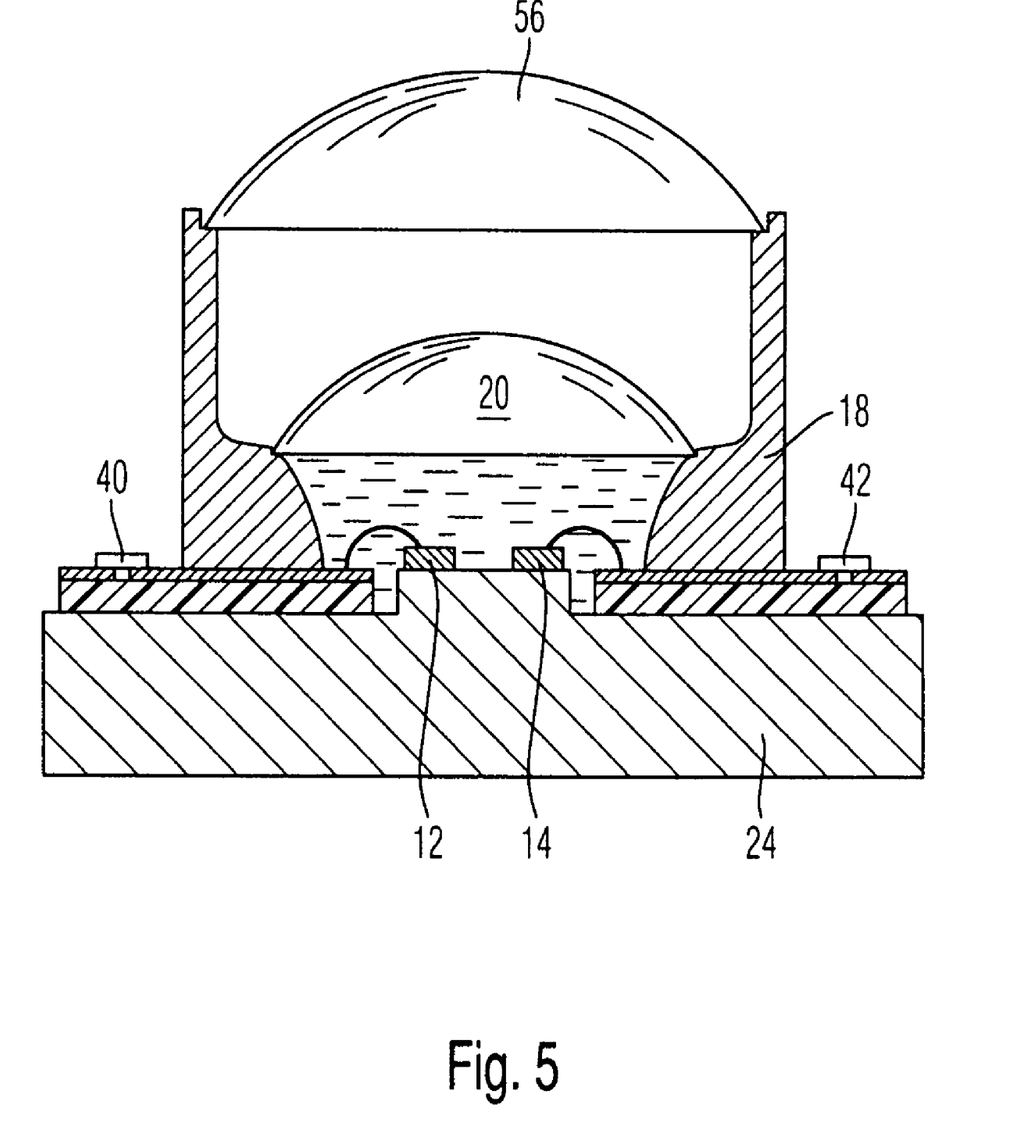
FIG. 5 shows a sectional and diagrammatic illustration of a third embodiment of an inventive radiation source.

Another modified refinement can be seen in FIG. 5. In the solution, the supporting element 18 has been considerably lengthened toward the front. In addition to the lens 20, said supporting element holds a converging lens 56 whose diameter considerably exceeds the diameter of the lens 20 and which in turn is arranged in front of the lens 20 in the form of a planoconvex lens. The dual arrangement of the lens 20 with the lens 56 makes it possible to focus the light emission to an even greater extent.

Figure 6:
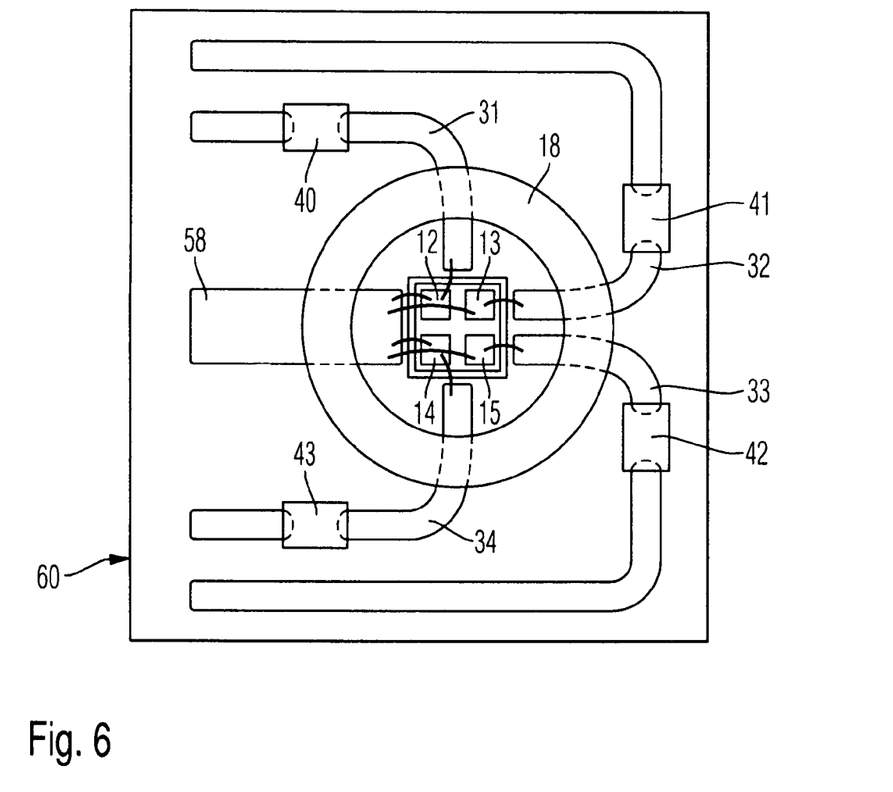
FIG. 6 shows the plan view of a fourth embodiment of an inventive radiation source.

Another refinement of an inventive semiconductor radiation source can be seen in FIG. 6. In this solution, provision is made of a plurality of LED chips 12, 13, 14, 15 which are arranged in a type of square. In this case, the LED chips have respective bonding wires on their top side, said wires being led to a ground conductor track 58, on the one hand, and establishing connections to conductor tracks 31, 32, 33, 34, on the other hand. In this case, the conductor tracks 31 to 34 are in turn formed on a printed circuit board 30 and extend, with connecting panels, into the internal space 16 of a supporting element 18. They run under the supporting element 18 and each terminate at an associated series resistor 40, 41, 42, 43, all of the series resistors being able to be adjusted. This is diagrammatically illustrated for the series resistors 42 and 43 using a constriction which can be seen there. In this refinement, further conductor tracks are arranged in such a manner that it is possible to make contact with one side 60 of the conductor track. This can be readily implemented in printed circuit boards in a manner known per se.

Figure 7:
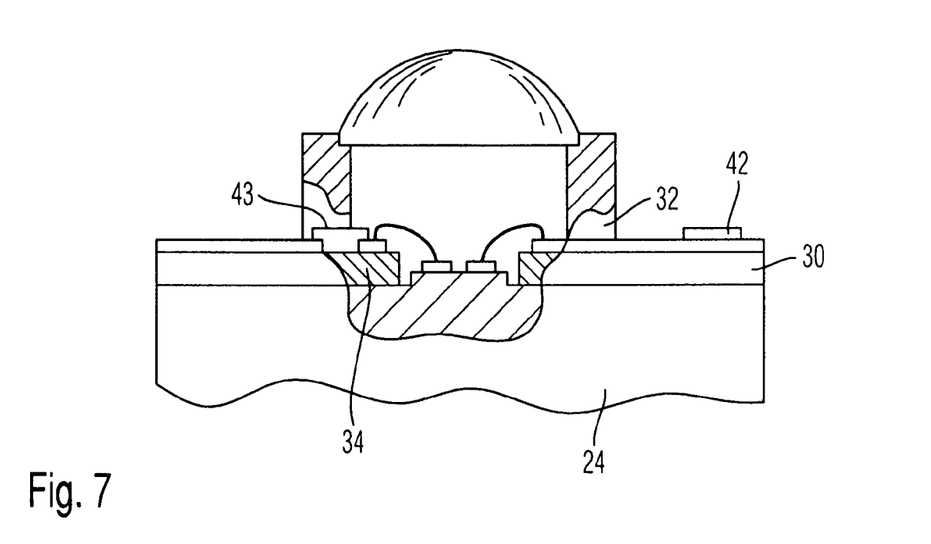
FIG. 7 shows a side view (partially cut away) of the embodiment shown in FIG. 6.

It can be seen in FIG. 7 that the conductor tracks 32 and 34 each extend on the printed circuit board 30. However, it is also equally possible, on the other hand, to use a printed circuit board using multilayer technology or to allow the conductor tracks to run at any desired point of the height of the printed circuit board via plated-through holes. In the case of conductor tracks which are arranged on the top side, provision is preferably made of a protective resist which covers the printed circuit board overall, that is to say including the conductor tracks and the series resistors 40 to 43. It goes without saying that this protective resist is applied only after the series resistors have been adjusted.

Figure 8:
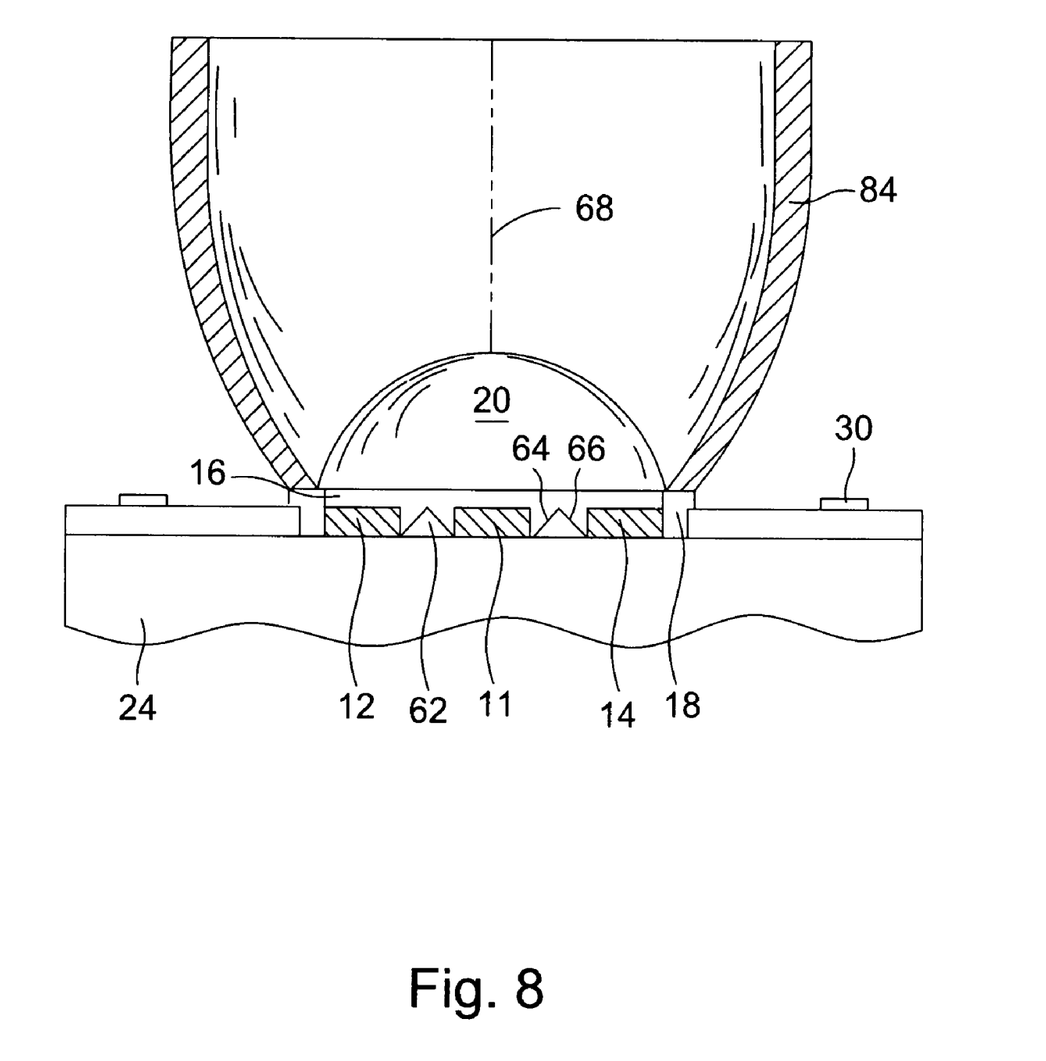
FIG. 8 shows a section through a fifth embodiment of an inventive radiation source.
Figure 9:
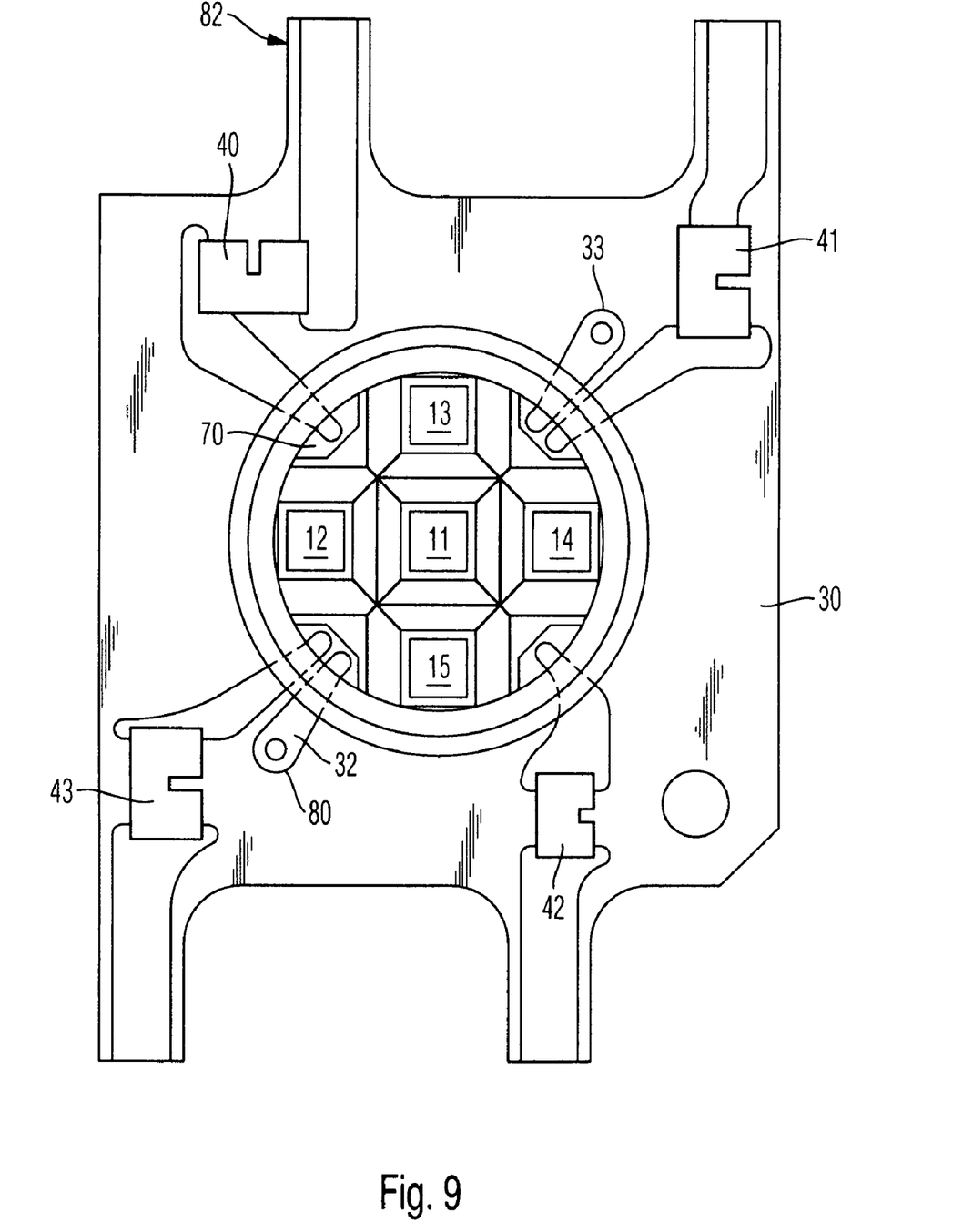
FIG. 9 shows a plan view of the embodiment shown in FIG. 8.

Another preferred embodiment can be seen in FIGS. 8 and 9. This embodiment has a somewhat more compact arrangement of the lens 20. In this embodiment, the supporting element is partially supported on the printed circuit board 30 and is partially supported on the base body 24 directly. Provision is made of a total of five LED chips 11, 12, 13, 14 and 15 which, as can be seen in FIG. 9, essentially extend in the manner of a cross. A grating reflector 62 which, for example, may be in the form of a small plastic body which is inserted into the multiple arrangement of the LED chips or is equally used as a spacer for the latter extends between the LED chips 11 to 15. Said grating reflector has reflector surfaces 64 and 66 which run obliquely, extend on the four side edges of the square chip, for example for the LED chip 11, and cast the laterally emitted light forward. This makes it possible to further increase the luminous efficiency of the light which has been focused in the lens 20. The grating structure of the grating reflector 62 extends outward in the form of fingers in a manner corresponding to the cross, as can be seen in FIG. 9. The printed circuit board 30 extends into the internal space 16 in the free corners of the cross. Six connecting panels 70 which are each used to supply power to the chips 11 to 15 can thus be provided for the exemplary embodiment illustrated, the wiring being implemented using bonding wires which, for the sake of clarity, are not illustrated in FIGS. 8 and 9.

As can be seen from the illustration shown in FIG. 9, conductor tracks 32, 33 of the six conductor tracks which have been provided in this manner terminate in contact vias 80 and are passed on in another level of the multilayer printed circuit board 30, for example to the underside of two of the four connecting lugs 82, in order to supply power to the semiconductor radiation source.

The compact arrangement of the chips which is particularly favorable according to the invention can be implemented in this case too, and adjustment is effected using series resistors 40 to 43 which can be calibrated. In this solution, provision is made for the radiation source to be operated with virtually two channels, the central LED chip 11 radiating at one frequency and the further LED chips 12 to 15 radiating at another frequency. There is therefore no need to adjust the LED chip 11 since only the LED chips 12 to 15 are connected in parallel with one another but it may additionally be provided for, if required, by implementing a fifth series resistor.

In the embodiment which can be seen in FIGS. 8 and 9, provision is additionally made of a reflector 84 which extends from the actual semiconductor radiation source and has a slightly curved surface in a manner known per se. The reflector 84 is then used to radiate any radiation which still emerges laterally, despite the high level of focusing by the lens 20, to the front in an improved manner.

The inlet end of a light guide (not illustrated in the figures) extends at a distance from said reflector in front of the converging lens 20 in the optical axis 68.

Figure 10:
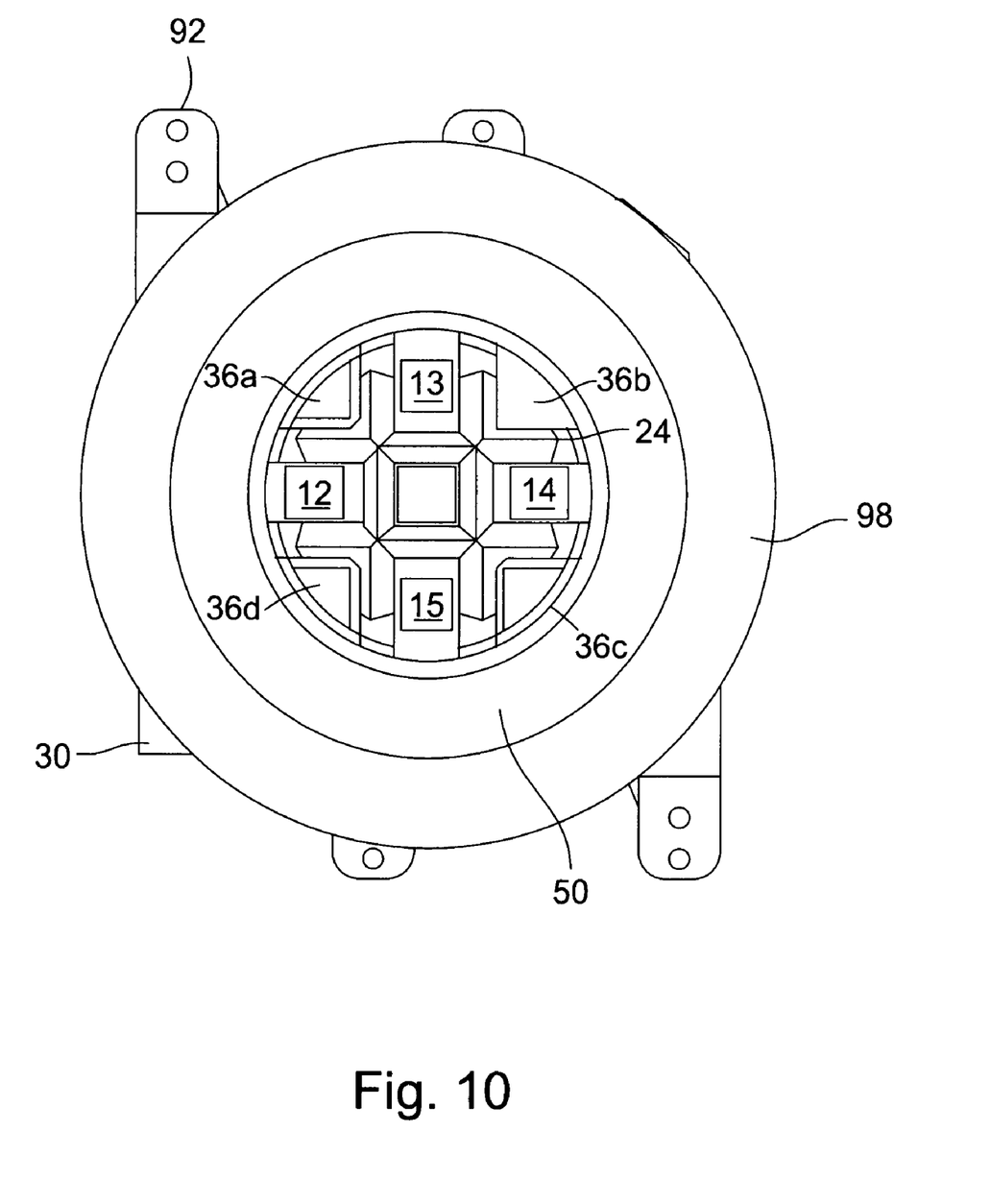
FIG. 10 shows a plan view of part of an inventive radiation source.
Figure 11:
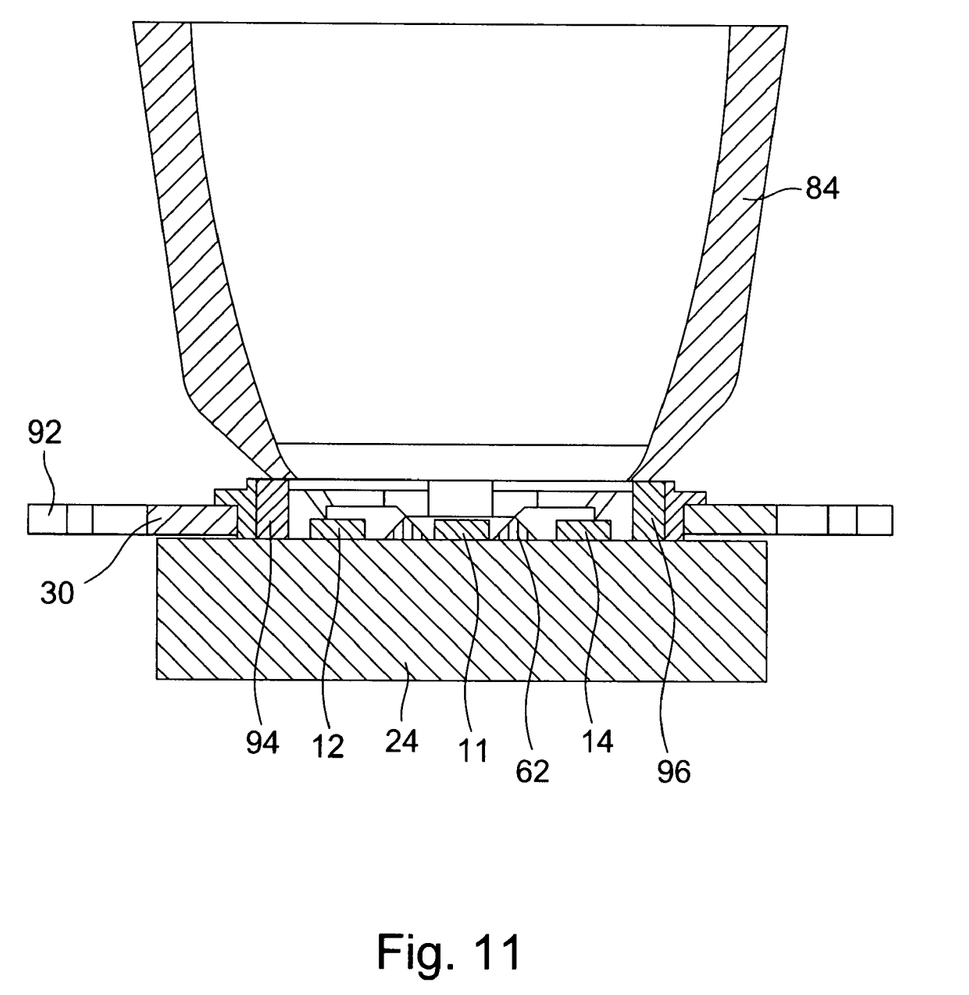
FIG. 11 shows a plan view of the embodiment shown in FIG. 10.

Another embodiment can be seen in FIGS. 10 and 11. Identical or similar reference symbols refer to identical or similar parts there and in the further FIGS. In this solution, five LED chips 11 to 15 are again essentially arranged in the form of a cross, with the result that the chips 12 to 15 surround a central chip 11. The chips are each surrounded by reflector elements 62 which extend between said chips and beside the latter and form part of a spacer which supports a reflector 84 in front of the LED chips.

In the plane of the drawing beneath the reflector 84 and as can be better seen in FIG. 11, provision is made of radiation absorbers 94 and 96 which extend between the external LED chips 12 and 14, on the one hand, and the printed circuit board 30. This solution is particularly favorable when high-energy radiation needs to be intercepted without impairing the printed circuit board. The radiation absorbers 94 and 96 may be applied to the base body 24 in the form of solid bodies, for example using an extremely thin adhesive layer, also similar to the chips themselves, so that good heat dissipation is ensured.

The radiation absorbers 94 and 96, of which two corresponding radiation absorbers are of course likewise provided for the further LED chips 11 and 15, may be composed of any desired suitable materials. Plastic bodies, aluminum bodies but also preferably ceramic bodies which may also be dyed dark in order to ensure even better radiation absorption are suitable, for example.

In the exemplary embodiment illustrated in FIG. 10, the printed circuit board 46 is also covered by a protective ring 98 which is likewise used for better protection, in particular of the calibration resistors, since calibration can be impaired as a result of excessive heating of the calibration resistors.

It goes without saying that the protective ring 98 is dimensioned in such a manner that the connecting tracks 92 remain free, the protective ring preferably being configured to be electrically insulating at least on its underside.

It can be seen in FIG. 11 that the LED chips 12, 11, and 14 are each also arranged at a distance from the reflector element. This also contributes to preventing the intensive emission of heat by the LED chips from becoming intensive application of heat to the grating reflector 62 which may be composed of plastic with mirrored surfaces.

Even if the illustration shown in FIG. 11 does not illustrate a lens corresponding to the cover lens 20, it goes without saying that said lens may be provided there in any desired suitable manner.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A semiconductor radiation source having:
a base body;

at least two centrally arranged LED chips directly mounted to the base body using a thermally conductive connection, wherein at least one LED chip is connected to an adjustable resistor; and at least one printed circuit board mounted on the base body, and wherein said adjustable resistor is mounted on the printed circuit board.

2. The radiation source as claimed in claim 1, wherein the printed circuit board projects into free areas which extend laterally beside the chips.

3. The radiation source as claimed in claim 2 wherein the printed circuit board is arranged between the edge of the base body and the LED chips.

4. The radiation source as claimed in claim 1, wherein a first LED chip is arranged on an optical axis and a plurality of further LED chips are radially arranged outside the first LED chip in such a manner that they are symmetrical with respect to one another and surround the first LED chip in the manner of a cross or star.

5. The radiation source as claimed in claim 4, wherein the printed circuit board also extends into the areas located between the limbs of the cross.

6. The radiation source as claimed in claim 1, wherein a reflector element is arranged between two mutually adjacent LED chips, and is supported on the base body and/or the printed circuit board and/or the LED chips.

7. The radiation source as claimed in claim 6, wherein the reflector element has two reflecting areas which run essentially obliquely, each reflecting area reflecting radiation emanating from the adjacent LED chip.

8. The radiation source as claimed in claim 7, wherein the reflecting areas, when viewed in the direction of the optical axis, essentially extend in a manner corresponding to the height of the printed circuit board or project beyond the printed circuit board and are of slightly concave or parabolic shape.

9. The radiation source as claimed in claim 1, wherein a plurality of reflector elements are connected to one another so as to form a grating reflector, the grating reflector being supported on the base body and/or the printed circuit board and/or the LED chips.

10. The radiation source as claimed in claim 1, wherein the LED chips are fitted in a central region of the base body, essentially at the height of to printed circuit board.

11. The radiation source as claimed in claim 1, wherein radiation absorbers which are connected to the base body using thermally conductive connections extend between external LED chips, and the printed circuit board.

12. The radiation source as claimed in claim 11, wherein the radiation absorbers extend at least over the width of the LED chips and have a greater height than the LED chips, preferably approximately 1.5 to 5 times the height, and particularly preferably approximately twice the height, of the LED chips.

13. The radiation source as claimed in claim 12, wherein a closed space which has a transparent or translucent liquid or gelatinous substance which extends between the LED chips, the spacer and the cover lens.

14. The radiation source as claimed in claim 11, wherein the radiation absorbers are simultaneously of heat-insulating design and are composed of ceramic.

15. The radiation source as claimed in claim 1, wherein a cover lens is arranged in the beam path downstream of the LED chips and an annular or tubular spacer is provided for said lens, and wherein the spacer is supported on the printed circuit board and/or the base body.

16. The radiation source as claimed in claim 15, wherein at least one conductor track of the printed circuit board runs through under the spacer.

17. The radiation source as claimed in claim 15, wherein a converging lens whose diameter is larger than the diameter of the cover lens is arranged in the beam path downstream of the cover lens.

18. The radiation source as claimed in claim 15, wherein a reflector is arranged in the beam path downstream of the LED chips at a distance from the latter and is also arranged downstream of the cover lens in the beam path.

19. The radiation source as claimed in claim 18, wherein a light guide is arranged in the beam path downstream of the reflector.

20. The radiation source as claimed in claim 1, wherein the base body is at least partially composed of copper and/or is at least partially coated with gold or nickel/gold.

21. The radiation source as claimed in claim 1, wherein the LED chips emit light at different wavelengths.

22. The radiation source as claimed in claim 1, wherein said printed circuit board extends away from the centrally arranged LED chips to the outside, to the peripheral region of the base body.

23. The radiation source as claimed in claim 1, wherein the at least one series resistor extends from the LED chips to the printed circuit board.

24. The radiation source as claimed in claim 23, wherein the series resistors are filled such that they are freely accessible outside the supporting element and can be adjusted there.

25. The radiation source as claimed in claim 24, wherein the series resistors are connected to the printed circuit board via resistance contact areas.

26. The radiation source as claimed in claim 24, wherein the series resistors are in the form of a resistance track whose width can be reduced, at least one point for example by means of laser trimming to change the resistance of the resistor.

27. The radiation source as claimed in claim 24, wherein the series resistor is printed onto the printed circuit board or is applied using thick-film technology and has a compound or paste containing conductive particles composed of graphite.

* * * * *